(12) United States Patent
Yamanishi et al.

(10) Patent No.: US 10,538,728 B2
(45) Date of Patent: Jan. 21, 2020

(54) BUBBLE-JETTING MEMBER, GAS-LIQUID JETTING MEMBER, LOCALIZED ABLATION DEVICE, AND LOCALIZED INJECTION DEVICE

(71) Applicant: JAPAN SCIENCE AND TECHNOLOGY AGENCY, Kawaguchi-shi, Saitama (JP)

(72) Inventors: Yoko Yamanishi, Tokyo (JP); Kazuki Takahashi, Tokyo (JP); Shun Omi, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 0 days.

(21) Appl. No.: 15/512,631

(22) PCT Filed: Nov. 4, 2015

(86) PCT No.: PCT/JP2015/080998
§ 371 (c)(1),
(2) Date: Mar. 20, 2017

(87) PCT Pub. No.: WO2016/072408
PCT Pub. Date: May 12, 2016

(65) Prior Publication Data
US 2017/0292105 A1 Oct. 12, 2017

(30) Foreign Application Priority Data
Nov. 7, 2014 (JP) .................................. 2014-226699

(51) Int. Cl.
*C12M 1/42* (2006.01)
*A23L 13/50* (2016.01)
(Continued)

(52) U.S. Cl.
CPC ............... *C12M 35/04* (2013.01); *A01G 7/06* (2013.01); *A23L 13/50* (2016.08); *A23L 13/72* (2016.08);
(Continued)

(58) Field of Classification Search
CPC ... A01G 7/06; A23L 13/50; A23L 13/72; A23V 2002/00; C12M 35/04; C12N 15/09; C12N 15/87
(Continued)

(56) References Cited

U.S. PATENT DOCUMENTS

| 6,913,605 B2 | 7/2005 | Fletcher et al. |
| 2010/0227408 A1* | 9/2010 | Vankov ................. C12N 13/00 435/461 |
| 2015/0011930 A1 | 1/2015 | Yamanishi et al. |

FOREIGN PATENT DOCUMENTS

| JP | WO2013129657 A1 | 9/2013 |
| JP | 5526345 B2 | 4/2014 |

OTHER PUBLICATIONS

European Patent Office, "Extended European Search Report," issued in European Patent Application No. 15 857 966.4 which is a European counterpart of patent family of U.S. Appl. No. 15/512,631 dated Aug. 11, 2017, 7 pgs.
(Continued)

*Primary Examiner* — Michael L Hobbs
*Assistant Examiner* — Liban M Hassan
(74) *Attorney, Agent, or Firm* — Amster, Rothstein & Ebenstein LLP (57) ABSTRACT

Provided is a bubble-jetting member, the tip section of which is not damaged even when high voltage is applied thereto. There can be provided a bubble jetting member comprising: a core that is formed of a conductive material; a shell part that is formed of an insulating material, includes an extended
(Continued)

section that extends beyond the tip of the core, and is closely adhered at least partially to the core and covers the core; and a space that is formed between the extended section and the tip of the core and has a bubble-jetting port, wherein there is formed on the tip of the extended section a thick portion that is thicker than the rest of the extended section whereby the tip section is not damaged.

8 Claims, 8 Drawing Sheets (51) Int. Cl.
 *A23L 13/70* (2016.01)
 *A01G 7/06* (2006.01)
 *C12N 15/87* (2006.01)
 *C12N 15/09* (2006.01)
(52) U.S. Cl.
 CPC .......... *C12N 15/87* (2013.01); *A23V 2002/00* (2013.01); *C12N 15/09* (2013.01)
(58) Field of Classification Search
 USPC ...................................................... 435/285.3
 See application file for complete search history.

(56) References Cited

OTHER PUBLICATIONS

Korean Patent Office, Office Action in Korean Application No. 10-2017-7005872 (5 pp., 5 pp. English Translation), dated Mar. 20, 2018.

State Intellectual Property Office of People's Republic of China, First Office Action and First Examination Opinion Notice for Chinese Application No. 201580048276.X (7 pp., 6 pp. English translation), dated Aug. 3, 2018.

Federal Service for Intellectual Property (Rospatent), Official Action for Russian Federation Application No. 2017107156 (6 pp., 3 pp. English Translation), dated Oct. 13, 2017.

Federal Service for Intellectual Property (Rospatent), Search Report for Russian Federation Application No. 2017107156 (2 pp.), dated Oct. 12, 2017.

Yuta Arakawa, et al., Micro-processing under water by plasma-based cavitation, Proceedings of the 6th International Symposium on Micro-Nano Science and Technology of the Japan Society of Mechanical Engineers, Oct. 20-22, 2014, p. 21pm3-PM004, The Japan Society of Mechanical Engineers, Matsue, Japan.

Yoko Yamanishi, Needle Free Injector by Electrically Induced Bubbles, Journal of the Society of Automotive Engineers of Japan, Apr. 1, 2015, vol. 69, No. 4, pp. 86 to 87, The Society of Automotive Engineers of Japan, Tokyo, Japan.

Yoko Yamanishi, Kango no Gokan, Nurse Senka 2015, Apr. 11, 2015, vol. 35, No. 5, pp. 90 to 95, SMS Co., Ltd., Tokyo, Japan.

Kazuki Takahashi, et al., Mapping and Pattering of Biological Materials by electrically-induced bubbles, Journal of the Institute of Electronics, Information and Communication Engineers, Jul. 27, 2015, vol. 115, No. 170, pp. 17 to 20, The Institute of Electronics, Information and Communication Engineers, Tokyo, Japan.

International Searching Authority (ISA), English translation of the Written Opinion of the International Searching Authority for International Application No. PCT/JP2015/080998 (9 pages), dated Feb. 9, 2016.

China National Intellectual Property Administration, Second Office Action for Chinese Application No. 201580048276.X (3 pp., 3 pp. English translation), dated Nov. 21, 2019.

\* cited by examiner

BUBBLE-JETTING MEMBER, GAS-LIQUID JETTING MEMBER, LOCALIZED ABLATION DEVICE, AND LOCALIZED INJECTION DEVICE

BACKGROUND OF THE INVENTION

Field of the Invention

The present invention relates to a bubble-jetting member, a gas/liquid jetting member, a localized ablation device, and a localized injection device, and particularly relates to: a bubble-jetting member in which the tip of a conventional bubble-jetting member is processed to be thick whereby a bubble-jetting port is made smaller and the tip is unlikely to be damaged even when high voltage is applied thereto; a gas/liquid jetting member in which an outside shell part that is capable of relative movement with the bubble-jetting member is formed whereby the position of the bubble-jetting member when processing a process target can be adjusted easily; a localized ablation device that includes the bubble-jetting member or the gas/liquid jetting member; and a localized injection device that includes the gas/liquid jetting member.

Description of the Related Art

Advances in biotechnology witnessed in recent years have been accompanied by increasing demand for localized processing of cells and the like, involving making a hole in a cell membrane or wall, and removing the nucleus from the cell, or introducing DNA or other nucleic acid substance into the cell. Methods employing a number of localized processing techniques (herein sometimes referred to as "localized ablation methods"), such as contact process techniques using a probe, such as an electric scalpel or the like, or non-contact ablation techniques employing lasers or the like, are widely known.

However, in conventional contact process techniques employing a probe such as an electric scalpel, there was a tendency for the target to be burned away due to Joule heat generated by continuous high frequencies, resulting in significant roughness at the incision face and in surrounding tissue being significantly affected by thermal invasion due to heat, and damage to the incision face due to heat is appreciable, particularly in processing of biomaterials in liquid phase (Problem 1); rejoining and regeneration were difficult, due to denaturation of proteins and/or fragmentation of amide bonds (Problem 2); and with continuous processing, adsorption onto the probe of heat-denatured proteins and/or adsorption of bubbles generated by heat resulted in the problem of marked degradation of the observation environment at the incision face, making high-resolution processing difficult (Problem 3).

In non-contact process techniques employing lasers such as femtosecond lasers and the like as well, there is an effect of heat on tissue surrounding the incision face by localized bombardment with high-density energy, and particularly during processing of a target in the liquid phase, generation of bubbles and the like due to heat generated during processing made continuous processing difficult.

Meanwhile, electroporation, sonoporation techniques employing ultrasound, particle gun methods, and the like are widely known as localized physical injection techniques (injection methods) for introducing nucleic acid substances or the like into cells or the like. However, in conventional electroporation techniques, depending on the electrical field strength, there are limits as to how much permeability of the cell membrane can be improved, making it difficult to inject targets having stiff cell membranes or cell walls, instead of pliable lipid bilayer membranes, and due to restrictions regarding electrode placement and the like, localized injection at the intended site was difficult. In sonoporation techniques employing ultrasound, it was difficult to focus the ultrasound, making it difficult to generate localized cavitation of bubbles and increase the resolution. In injection methods that rely on the particle gun method as well, the problem of low efficiency of introduction, due to separation of the substance deposited on the particle surface occurring when the particle is shot in was encountered.

In order to solve the abovementioned problems, the present inventors newly discovered that cutting (localized ablation) of a process target can be performed by: producing a bubble-jetting member comprising a core that is formed of a conductive material, a shell part that is formed of an insulating material, covers the core, and includes a section extending from the tip of the core, and a space that is formed between the extended section of the shell part and the tip of the core; immersing the bubble-jetting member in a solution; applying a high-frequency voltage to the solution to produce bubbles; and continuously ejecting the bubbles onto the process target. Furthermore, it was newly discovered that bubbles in which a solution of dissolved and/or dispersed injection material is adsorbed on the interfaces thereof can be produced by providing an outside shell part on the outside of the shell part of the bubble-jetting member so as to leave a space with the shell part, and introducing a solution of dissolved and/or dispersed injection material into the space; and a process target can be cut and the injection material contained in the solution covering the bubbles can be injected into the process target by continuously ejecting the bubbles onto the process target. An application for patent was thus filed (see Patent Document 1).

PRIOR ART DOCUMENTS

Patent Documents
[Patent Document 1] Japanese Patent 5526345

SUMMARY OF THE INVENTION

Problems to Be Solved by the Invention

When localized ablation is performed using the bubble-jetting member described in Patent Document 1, localized ablation can be performed when the process target is cells or other soft material. Meanwhile, when performing localized ablation on a comparatively hard process target, it may be necessary to apply high voltage to the bubble-jetting member in order to accelerate the speed of jetting of bubbles and increase the collision energy. However, a new problem arose that the tip section of the bubble-jetting member will be damaged when high voltage is applied to the bubble-jetting member described in Patent Document 1.

Also, when performing localized ablation on the process target, it is necessary to adjust the positional relationship with the process target while observing the bubble-jetting port of the bubble-jetting member under microscopy. However, a new problem arose that because the bubble-jetting member is made by pulling glass off, etc., the bubble-jetting port becomes sharp and the process target adversely affected during localized injection.

Furthermore, with the gas/liquid jetting member described in Patent Document 1, because the outside shell part is fitted on the outside of a positioning washer fitted on the bubble-jetting member, the distance between the bubble-jetting port of the bubble-jetting member and the tip of the outside shell part cannot be changed. Therefore, a new problem arose that bubbles in which a solution containing an injection material is adsorbed on the boundaries thereof (referred to below as "gas/liquid") lose energy by the time of reaching the process target, and the gas/liquid may be repelled by the process target depending on the process target. Therefore, although it may be necessary to raise the voltage applied to the bubble-jetting member to increase the collision energy of the gas/liquid, a new problem arose that the tip section of the bubble-jetting member gets damaged when high voltage is applied as mentioned above.

The present invention was contrived in order to solve the abovementioned problems, and after thoroughgoing research, it was newly discovered that: (1) by increasing the thickness of the tip of the extended section made by pulling apart an insulating material, the tip section is not damaged even when high voltage is applied to the bubble-jetting member; (2) because the tip section is thick, the process target is less likely to be pierced and damaged; (3) because the diameter of the bubble-jetting port is made smaller when the tip section is processed to a greater thickness, the process target can be processed more finely without the tip section becoming damaged; (4) producing the gas/liquid jetting member so that the bubble-jetting member and the outside shell part are capable of relative movement facilitates positional adjustment of the bubble-jetting member and the process target during localized ablation or localized injection; and (5) pressing the outside shell part against the process target can prevent leakage of the solution containing the injection material from the outside shell part, and allows the positional relationship between the bubble-jetting member and the process target to be adjusted in that state. Therefore, a localized ablation device or localized injection device including the gas/liquid jetting member of the present invention can be used in atmospheric air and can be applied, for example, to a needleless injection device.

In other words, an object of the present invention is to provide a bubble-jetting member, a gas/liquid jetting member, a localized ablation device, and a localized injection device.

Means for Solving the Problems

The present invention relates to a bubble-jetting member, a gas/liquid jetting member, a localized ablation device, and a localized injection device as illustrated below.

(1) A bubble-jetting member, comprising:
a core that is formed of a conductive material;
a shell part that is formed of an insulating material, includes an extended section that extends beyond the tip of the core, and closely adheres at least partially to the core and covers the core; and
a space that is formed between the extended section and the tip of the core and has a bubble-jetting port;
there being formed on the tip of the extended section a thick portion that is thicker than the rest of the extended section.

(2) A gas/liquid jetting member, comprising: the bubble-jetting member according to (1) above; and
an outside shell part that is formed on the outside of the shell part of the bubble-jetting member and is formed in a position away from the shell part so that a space is left therebetween.

(3) The gas/liquid jetting member according to (2) above, wherein the outside shell part and the bubble-jetting member are formed so as to be capable of relative movement.

(4) The gas/liquid jetting member according to (3) above, wherein an end of the outside shell part is connected to the bubble-jetting member by way of an expansion/contraction member.

(5) The gas/liquid jetting member according to any of (2) to (4) above, wherein a constricted portion is formed on the outside shell part, the constricted portion serving as a guide during relative movement between the outside shell part and the bubble-jetting member.

(6) The gas/liquid jetting member according to any of (2) to (5) above, further comprising:
a counter electrode that, together with the core of the gas/liquid jetting member, constitutes a pair of electrodes,
the counter electrode being formed on the outer surface of the shell part or on the inner surface of the outside shell part.

(7) The gas/liquid jetting member according to any of (2) to (6) above, wherein the tip section of the outside shell part is formed thicker than the rest of the outside shell part.

(8) A localized ablation device, comprising the bubble-jetting member according to claim 1 or the gas/liquid jetting member according to any of (2) to (7) above.

(9) A localized injection device, comprising the gas/liquid jetting member according to any of (2) to (7) above.

Effects of the Invention

Because the tip section of the bubble-jetting member of the present invention is of increased thickness, the tip section of a localized ablation device using the bubble-jetting member or gas/liquid jetting member of the present invention is less likely to be damaged even when high voltage is applied thereto. Accordingly, the collision energy of the jetted bubbles can be increased, and localized ablation can accordingly be performed even on harder process targets. Also, because the bubble-jetting port of the bubble-jetting member can be made smaller when thickness-increasing processing is performed, the process target can be finely processed. Furthermore, because the tip of the bubble-jetting member can be formed flat, the process target is less likely to be adversely affected during localized injection.

The gas/liquid jetting member of the present invention is produced so that the bubble-jetting member and the outside shell part are capable of relative movement. Accordingly, positional adjustment of the process target and the bubble-jetting portion can be performed easily when performing localized ablation or localized injection on the process target using a localized ablation device or a localized injection device using the gas/liquid jetting member of the present invention. Furthermore, pressing the outside shell part against the process target during positional adjustment can prevent leakage of a conductive solution or a solution containing an injection material, and allows the positional relationship between the bubble-jetting member and the process target to be adjusted in that state. Therefore, the localized ablation device or the localized injection device of the present invention can be used in open air, and accordingly can be used, for example, as a needleless injection device.

BRIEF DESCRIPTION OF THE DRAWINGS

FIG. 6 is a photograph substituting for a drawing; FIG. 6(1) is a photograph of the tip section of the bubble-jetting member 1 produced in example 1.

FIG. 8 is a photograph substituting for a drawing.

FIG. 10 is a photograph substituting for a drawing.

FIG. 11 is a photograph substituting for a drawing.

FIG. 12 is a photograph substituting for a drawing.

DESCRIPTION OF THE PREFERRED EMBODIMENTS

Figure 1:
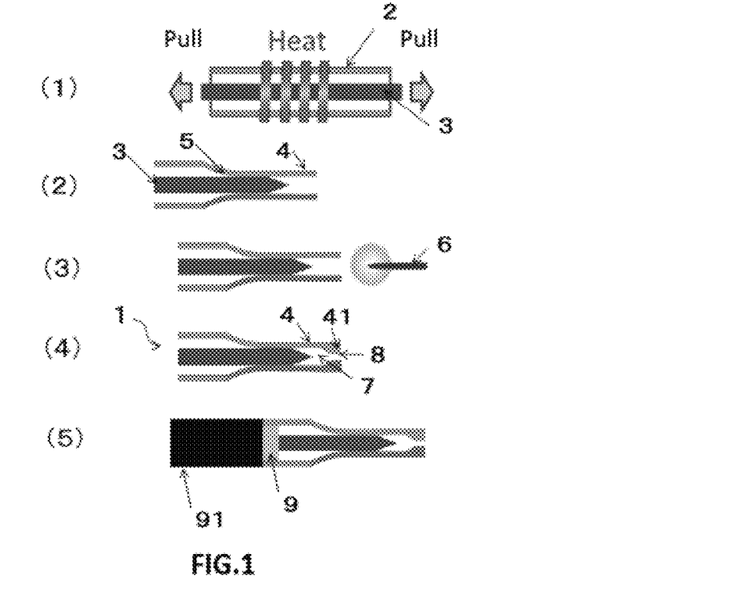
FIG. 1 illustrates one example of the method of production of the bubble-jetting member 1 of the present invention.

FIG. 1 illustrates one example of the method of production of the bubble-jetting member 1 of the present invention. The bubble-jetting member 1 of the present invention can be formed by the following procedure.

(1) A hollow insulating material 2 is prepared, a core 3 formed of a conductive material is inserted into the hollow insulating material 2, and the combined material is applied with heat and pulled apart.

(2) Due to a difference in viscoelasticity between the insulating material 2 and the core 3, a shell part 5 that includes an extended section 4 in which the insulating material 2 further extends from the tip of the core 3 is formed so as to adhere closely to the outer perimeter of the core 3.

(3) Heating means 6 are arranged on the tip of the extended section 4, and are pressed against the extended section 4.

(4) A thick portion 41 is formed on the tip of the extended section 4, and thus it is possible to produce a bubble-jetting member 1 that includes a space 7 that is formed between the tip of the core 3 and the extended section 4 and has a bubble-jetting port 8.

(5) The periphery of the core 3 may be packed with a conductive material 9 and an insulating material 91 may be used to cover the periphery in order to facilitate connection to an electrode of a localized ablation device or localized injection device.

There are no particular limitations as to the insulating material 2 provided it is one that insulates electricity; for example, there can be cited glass, mica, quartz, silicon nitride, silicon oxide, ceramics, alumina, and other such inorganic insulating materials, silicone rubber, ethylene propylene rubber, and other such rubber materials, ethylene vinyl acetate copolymer resins, silane-modified olefin resins, epoxy resins, polyester resins, vinyl chloride resins, acrylic resins, melamine resins, phenolic resins, polyurethane resins, polystyrene resins, fluororesins, silicone resins, polysulfide resins, polyamide resins, polyimide resins, polyethylene, polypropylene, cellulose resins, UV-curing resins, and other such insulating resins.

The conductive material forming the core 3 is not particularly limited, provided that the material can be used as an electrode. A metal is preferred, examples of which including gold, silver, copper, aluminum, and the like, as well as alloys to which small amounts of tin, magnesium, chromium, nickel, zirconium, iron, silicon, or the like, have been added. As described above, the space 7 is formed by the tip of the core 3 and the extended section 5 in which the insulating material 2 is extended further out from the tip of the core, and therefore any combination of suitable materials such that the viscoelasticity of the insulating material 2 is greater than the viscoelasticity of the core 3 is acceptable. Examples of a combination of the insulating material 2 and the core 3 include glass and copper, glass and platinum, glass and aluminum, glass and gold, glass and silver, glass and nickel, epoxy resin and copper, epoxy resin and platinum, epoxy resin and aluminum, epoxy resin and gold, epoxy resin and silver, epoxy resin and nickel, acrylic resin and copper, acrylic resin and platinum, acrylic resin and aluminum, acrylic resin and gold, acrylic resin and silver, acrylic resin and nickel, silicone resin and copper, silicone resin and platinum, silicone resin and aluminum, silicone resin and gold, silicone resin and silver, and silicone resin and nickel.

When bubbles are to be jetted using the bubble-jetting member 1, electricity is outputted, whereupon bubbles formed at one end are jetted from the bubble-jetting port 8 so as to be pulled apart in the space 7 as later described. Accordingly, there is no need to feed gas from the exterior to the bubble-jetting member 1. Consequently, the core 3 of the present invention is formed in a solid state in which the conductive material has been extended, and a tube or the like for feeding air to the interior of the core 3 is not formed, as shown in FIG. 1. At least a portion of the shell part 5 is configured so as to closely adhere to the core 3 near the tip of the bubble-jetting member 1 due to the difference in viscoelasticity between the insulating material 2 and core 3.

The size of the jetted bubbles can be adjusted by changing the diameter of the bubble-jetting port 8. When using the localized ablation device or localized injection device, a solution that passes electricity by capillary action (referred to below as a "conductive solution") must be filled in the space 7 of the bubble-jetting member 1. Therefore, the diameter of the bubble-jetting port 8 must be a size sufficient for the conductive solution to pass through by a capillary phenomenon, and about 100 nm or larger is preferred, 200 nm or larger is more preferred, and 500 nm or larger is particularly preferred. Meanwhile, the upper limit is not particularly limited provided that the range is such that bubbles can be jetted and a process target is not damaged, but when used for ablation of cells or injection in animals, etc., about 100 μm or smaller is preferred, 50 μm or smaller is more preferred, and 15 μm or smaller is particularly preferred. The diameter of the bubble-jetting port 8 can be adjusted by the temperature and speed of pulling apart when heating and the condition of pressing of the heating device 6.

The heating device 6 are not particularly limited provided that increased-thickness processing is possible by heating to a temperature at or above the melting point of the insulating material 2 and pressing while melting the tip section of the extended section 4. For example, a microforge or another publicly known device should be used. Pulled apart insulating material 2 has been directly used for the extended section 4 of conventional bubble-jetting members. Therefore, the extended section 4 near the bubble-jetting port 8 decreases in thickness as the bubble-jetting port 8 is made smaller, and it is easier for the process target to be adversely affected. Furthermore, in order to improve the directionality of the jetted bubbles, the extended section is thin due also to the fact that pulling apart is done at a speed for the entirety of the extended section to become tapered.

Meanwhile, the size of the bubble-jetting port 8 of the bubble-jetting member 1 of the present invention can be adjusted by melting the tip section of the extended section 4 using the heating device 6. Accordingly, the core 3 and the insulating material 2 used can be larger than in the conventional bubble-jetting member 1. Also, by (1) stopping pulling in a state in which the bubble-jetting port 8 is larger than intended, that is, a state in which the core 3 can be pulled apart by pulling but the extended section 4 is thick prior to being pulled apart due to the difference of viscoelasticity, (2) forming an opening by cutting the extended portion, and (3) next melting the opening by the heating device 6 and forming a bubble-jetting port 8 while forming a thick portion, (4) the bubble-jetting port 8 can be made smaller while further assuring the thickness of the extended section 4. Accordingly, when producing a bubble-jetting member 1 having a bubble-jetting port 8 of the same size as the bubble-jetting port 8 of a conventional bubble-jetting member 1, the bubble-jetting member 1 of the present invention can have a thicker extended section 4 and durability can be improved. When forming the thick portion using a microforge, there is no limit to the shape of the thick portion because the tip section of the extended section 4 is less likely to be damaged if the tip section is of increased thickness, but increasing the thickness so that the inside of the extended section 4 is tapered going toward the tip is preferred because the directionality of the jetted bubbles can be increased.

In order to adopt a configuration to avoid adversely affecting a process target when performing localized ablation on the process target, it is desirable to make the extended section 4 of the bubble-jetting port 8 portion thick by heating and pushing in, and to process the surface contacting with the process target with the heating device 6 so as to become flat.

Figure 2:
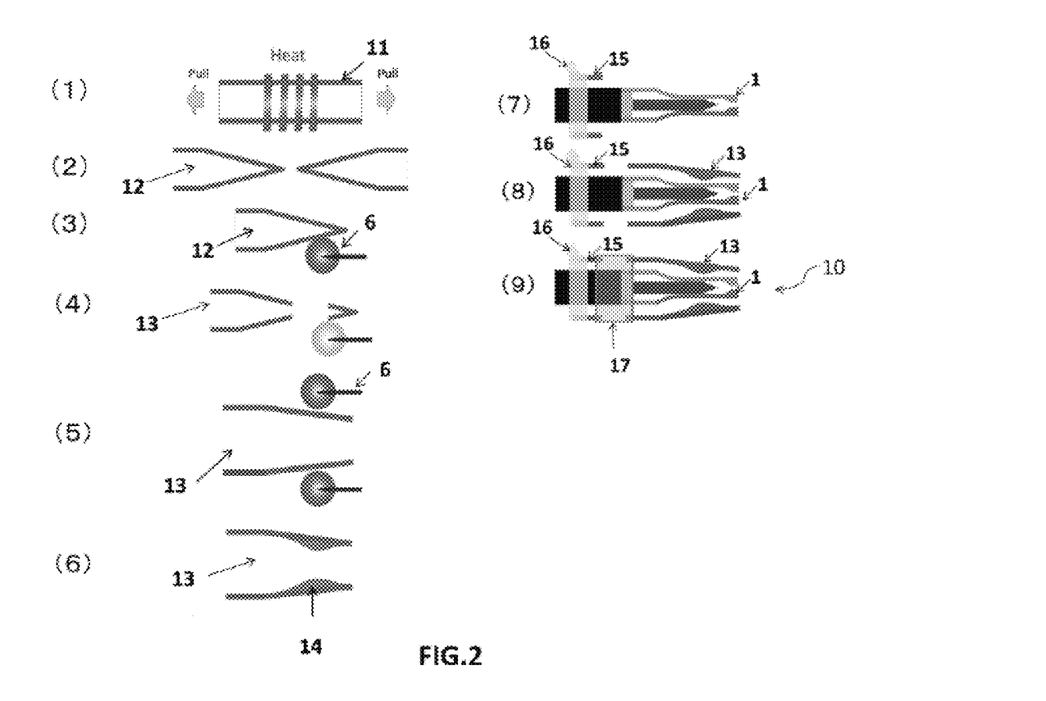
FIG. 2 illustrates one example of the production method in an embodiment of the gas/liquid jetting member 10 of the present invention.

FIG. 2 illustrates one example of the production method in an embodiment of the gas/liquid jetting member 10 of the present invention. The gas/liquid jetting member 10 illustrated in FIG. 2 can be formed by the following procedure.

(1) An insulating material 11 having a larger inner diameter than the hollow insulating material 2 illustrated in FIG. 1 is prepared, and then pulled while heat is being applied.

(2) The insulating material 11 is pulled apart, whereby a tube 12 having a sharp tip is produced.

(3) The tip section of the tube 12 is heated using heating device 6.

(4) The tip section of the tube 12 is cut, whereby an outside shell part 13 is produced. Although not illustrated, together with cutting of the tip section, a thick portion may be formed on the tip section of the outside shell part 13 by the same procedure as for the tip section of the extended section 4 of the bubble-jetting member 1.

(5) The heating device 6 are pressed against the outside shell part 13 in order to form a constricted portion to guide the bubble-jetting member 1 when the bubble-jetting member 1 performs relative movement with the outside shell part 13.

(6) The constricted portion 14 is formed on the outside shell part 13.

(7) A washer 16 having an embedded first ring 15 is fitted on the bubble-jetting member 1.

(8) The outside shell part 13 is inserted on the outside of the bubble-jetting member 1.

(9) The ends of the first ring 15 and the outside shell part 13 are connected by an expansion/contraction member 17, whereby the gas/liquid jetting member 10 is produced.

In the abovementioned steps, the constricted portion 14 should be formed as needed, and formation of the constricted portion 14 is not necessary.

The insulating material 11 may be the same material as that of the abovementioned insulating material 2. The constricted portion 14, when formed, is preferably formed to be in a symmetrical shape in at least three places in order to suppress shifting of position when the bubble-jetting member 1 moves. The first ring 15 should also be of the same material as that of the insulating material 2. The washer 16 should be produced by soft lithography or three-dimensional photolithography using a polymer film, silicon, rubber, or PDMS (polydimethylsiloxane). The expansion/contraction member 17 is not particularly limited provided that the expansion/contraction member 17 can be connected to the ends of the first ring 15 and the outside shell part 13 and can expand and contract to relatively move the bubble-jetting member 1 and the outside shell part 13, and examples include PDMS sheet, rubber, and springs. It is desirable that the expansion/contraction member 17 apply force in a direction of pushing so that the outside shell part 13 is positioned forward of the bubble-jetting port 8 in a state when not pressing against a process target, and therefore the expansion/contraction member 17 is preferably formed of a material that returns to an original shape when pressing is stopped.

Figure 3:
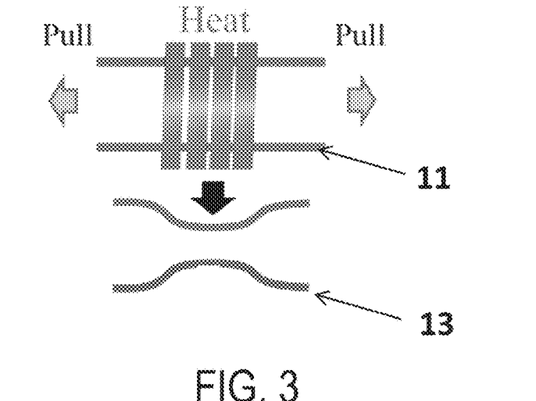
FIG. 3 illustrates another procedure for production of the outside shell part 13.

FIG. 3 illustrates another procedure for production of the outside shell part 13. The outside shell part 13 illustrated in FIG. 3 can be produced by applying heat to the insulating material 11 and pulling, and stopping in a state in which the heated portion has become somewhat larger than the diameter of the bubble-jetting member 1. A gas/liquid jetting member 10 of a different embodiment than in FIG. 2 can be produced by using the outside shell part 13 illustrated in FIG. 3 as the outside shell part 13 in (8) and (9) of FIG. 2. When the process target is very small, such as a cell, the gas/liquid jetting member 10 of the embodiment illustrated in FIG. 2 should be used. Also, when performing localized injection to humans or other animals, there is a possibility of injuring the human or animal if the opening portion of the outside shell part 13 is small, and therefore a gas/liquid jetting member 10 that includes an outside shell part 13 having a large opening portion as illustrated in FIG. 3 should be used.

In the production procedure illustrated in FIG. 2, the first ring 15 and the outside shell part 13 are connected to the expansion/contraction member 17, but there is no particular limitation provided that the structure is such that the bubble-jetting member 1 and the outside shell part 13 are capable of relative movement and the conductive solution filled between the bubble-jetting member 1 and the outside shell part 13 does not leak. For example, a second ring may be attached to the end of the outside shell part 13 and the first ring 15 and the second ring may be connected by the expansion/contraction member 17. Moreover, a first ring 15 may be not formed, and one end of the expansion/contraction member 17 may be adhered to the end of the outside shell part 13 and the other end of the expansion/contraction member 17 may be adhered to the bubble-jetting member 1. Also, the expansion/contraction member 17 is not limited to a single material and may be formed with combined materials. For example, the expansion/contraction member 17 may be formed by fitting a spring or other material having a space and being capable of expanding and contracting on the ends of the first ring 15 and the outside shell part 13 and fixing with an adhesive agent, and then sealing with a thin film so that the conductive solution does not leak around the spring, etc.

The statement that "the outside shell part and the bubble-jetting member are formed so as to be capable of relative movement" is not limited to the examples illustrated in FIG. 2 and FIG. 3, in which the outside shell part 13, being hard and having an unchanging shape, is connected by way of the expansion/contraction member 17 so that relative movement becomes possible with the bubble-jetting member 1, and there is no limitation in particular provided that the positional relationship between the end of the outside shell part 13 and the bubble-jetting port 8 of the bubble-jetting member 1 can be changed. For example, also possible is a structure in which the entirety of the outside shell part 13 is formed of a resin or other material and a portion thereof is formed like an accordion so that a portion of the outside shell part 13 easily expands and contracts. Also, the entirety of the outside shell part 13 may be formed with a flexible material so that the outside shell part 13 bulges outward by pressing against a process target and the position of the bubble-jetting member 1 can be adjusted.

The abovementioned gas/liquid jetting member 10 is formed so that the bubble-jetting member 1 and the outside shell part 13 are capable of relative movement, but because the bubble-jetting member 1 of the present invention exhibits superior performance to the conventional bubble-jetting member, it is sufficient to replace only the bubble-jetting member of a publicly known gas/liquid jetting member with the bubble-jetting member 1 of the present invention. In that case, for example, a polymer film or rubber washer, or a positioning washer produced by soft lithography or three-dimensional photolithography using PDMS (polydimethyl-siloxane) may be fitted on the bubble-jetting member 1 illustrated in FIG. 1, and the outside shell part 13 illustrated in FIG. 2 (5) or (6) may be fitted on the outside of the washer.

Figure 4:
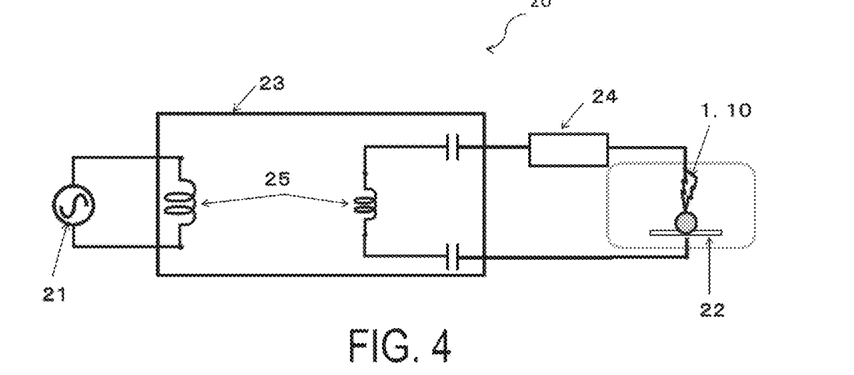
FIG. 4 illustrates the entirety of the localized ablation device 20.

FIG. 4 illustrates the overall configuration of a localized ablation device 20. The localized ablation device 20 includes electricity output device. The electricity output device includes at least a generic commercial AC power supply device 21, and an electric wire 23 for forming a circuit between the core 3 (active electrode) of the bubble-jetting member 1 or the gas/liquid jetting member 10 and the counter electrode 22, and may also have a non-dielectric resistor 24, a voltage amplification circuit 25, a digital input/output (DIO; not shown) port, etc., as needed. The electricity output device can be fabricated merely by incorporating a non-dielectric resistor 24, DIO port, etc. in a conventional electrical circuit for an electric scalpel, and setting to an output configuration for use on microscopic objects.

A counter electrode 22 may be formed separately from the bubble-jetting member 1 or gas/liquid jetting member 10, but when the gas/liquid jetting member 10 is used, the counter electrode 22 may be arranged on the outer surface of the shell part 5 or on the inner surface of the outside shell part 13. When the counter electrode 22 is provided on the gas/liquid jetting member 10, the counter electrode 22 should be capable of forming a circuit with the core 3, and therefore there is no limitation in particular provided that the counter electrode 22 comes in contact with the conductive solution filled between the shell part 5 and the outside shell part 13 of the bubble-jetting member 1. The counter electrode 22 should be of a material given as example with the core 3.

The current, voltage, and frequency output from the electricity output means to the core 3 and the counter electrode 22 are not particularly limited provided that the ranges are such that localized ablation or localized injection of a process target is possible and the bubble-jetting member 1 or gas/liquid jetting member 10 is not damaged, but for example, the current is preferably 1 mA to 10 A, more preferably 1 mA to 80 mA, and particularly preferably 2 mA to 75 mA. It is undesirable for the current to be smaller than 1 mA, since it may not be possible to produce bubbles favorably, or for the current ton ne greater than 10 A, wear of the electrode may occur, and that is not favorable. The voltage is preferably 0.1 V to 100 kV, more preferably 100 V to 1800 V, and particularly preferably 200 V to 1200 V., and that is not favorable It is undesirable for the voltage to be smaller than 0.1 V, since production of bubbles may be difficult, and if the voltage is greater than 100 kV, wear of the core 3 or damage to the bubble-jetting member 1 might occur. The frequency is preferably 0.1 kHz to 10 GHz, more preferably 1 kHz to 1 GHz, even more preferably 5 kHz to 1 MHz, and particularly preferably 10 kHz to 60 kHz. If the frequency is smaller than 0.1 kHz, the impact on the process target might be great and the bubble-jetting member 1 might be damaged, and if the frequency is greater than 10 GHz, it might not be possible to produce bubbles.

When using a localized ablation device, the bubble-jetting member 1 or gas/liquid jetting member 10 and the counter electrode 22 should be immersed in a conductive solution and voltage should be applied. The process target is not particularly limited provided that holes can be opened or the object can be cut by colliding with bubbles. Examples include stem cells isolated from human or non-human animal tissues, skin cells, mucous cells, liver cells, islet cells, nerve cells, cartilage cells, endothelial cells, epithelial cells, bone cells, muscle cells, egg cells, etc., and plant cells, insect cells, *E. coli*, molds, and other microbial cells, and other cells, and proteins and other organic crystals.

In Patent Document 1, the present inventors demonstrated that bubbles jetted from the bubble-jetting member could adsorb an injection material. Presumably, the bubbles produced by energizing the core 3 are charged with electricity, and the injection material is adsorbed onto the bubbles due to the electricity. Accordingly, when performing localized ablation using the gas/liquid jetting member 10, if an injection material is caused to be contained in the conductive solution in which the gas/liquid jetting member 10 is immersed, bubbles around which the injection material is adsorbed can be jetted. Therefore, the injection material can be introduced while performing localized ablation on the process target.

The injection material is not particularly limited, whether gas, solid, or liquid, provided that the material can be dissolved and/or dispersed in a solution. Examples of gases include air, nitrogen, helium, carbon dioxide, carbon monoxide, argon, and oxygen; and examples of liquids include solutions containing DNA, RNA, proteins, amino acids, and other biomolecules, and chemical solutions.

Figure 5:
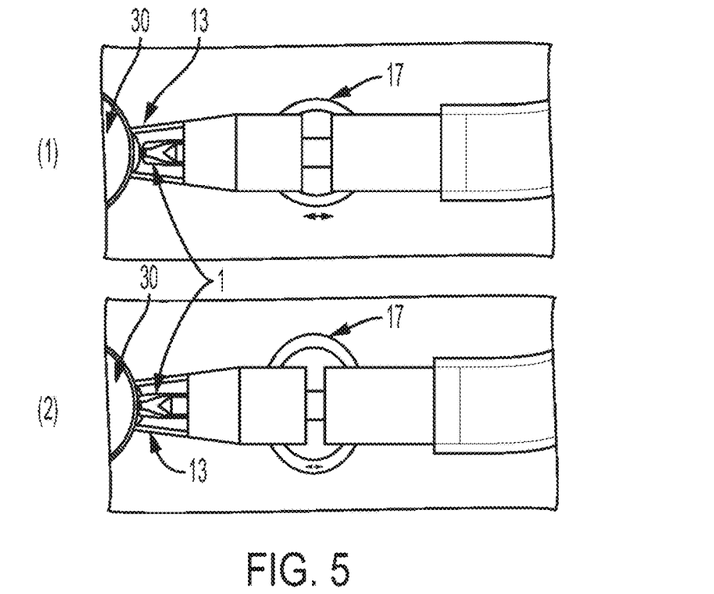
FIG. 5 illustrates one example in an embodiment of the localized injection device of the present invention.

FIG. 5 illustrates one example in an embodiment of the localized injection device of the present invention. The localized injection device of the present invention also can be used by immersing the gas/liquid jetting member 10 in a conductive solution in the same manner as in the prior art. However, with the gas/liquid jetting member 10 of the present invention, a solution containing an injection material (referred to below as "injection solution") is filled in the space inside the outside shell part 13 of the gas/liquid jetting member 10 so that the injection solution does not leak to the outside by bringing into contact with an object of processing 30, as illustrated in FIG. 5(1). Also, the bubble-jetting member 1 can be pushed in and the bubble-jetting port 8 can be arranged in a position suitable for localized injection, as illustrated in FIG. 5(2). Accordingly, the localized injection device of the present invention can be used in open air.

Furthermore, since high voltage can be applied owing to the thick portion 41 being formed on the extended section 4 of the bubble-jetting member 1 as mentioned above, use is possible also for localized injection to cells, as well as animals, etc., as in the prior art. Also, because the localized injection device of the present invention can be used in open air and can be applied with high voltage, use is possible as a needleless injection device. In particular, the conventional injection device using an injection needle has problems including infliction of pain from piercing with the needle as well as transmission of viruses from reuse or mistakenly piercing with a used needle, but the abovementioned problems can be solved by using the localized injection device of the present invention as a needleless injection device.

Filling of the injection solution into the space inside the outside shell part 13 of the gas/liquid jetting member 10 may be done by immersing the tip of the gas/liquid jetting member 10 in the injection solution and filling by capillary action, or by connecting a tube, etc., to the space between the bubble-jetting member 1 and the outside shell part 13 and injecting therein.

The present invention is described specifically below with examples, but these examples are provided simply for reference to specific embodiments for description of the present invention. Although these illustrations are for describing specific embodiments of the present invention, they do not represent restrictions or limitations on the scope of the present invention disclosed in the present application.

EXAMPLES

[Production of Bubble-Jetting Member 1]

Example 1

Figure 6:
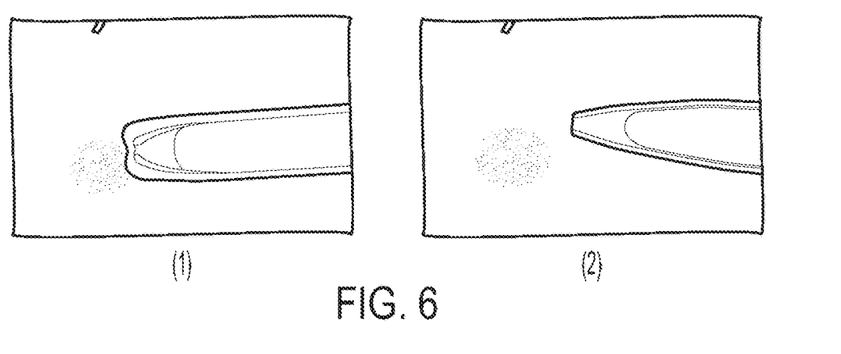
FIG. 6(2) is a photograph of the tip section of the bubble-jetting member 1 produced in comparative example 1.

Cu wire having a diameter of 30 μm was inserted into a borosilicate glass tube for micropipettes (outer diameter 1.37 mm, inner diameter 0.93 mm, Drummond Scientific Company), and the glass tube was pulled apart under heating using a glass puller (P-1000IVF, product of Sutter Co.), whereby the glass was stretched from the Cu wire. Next, a thick portion was formed by pushing in the tip section of the stretched glass while melting using a microforge (MF-900, Narishige Co.), and a bubble-jetting member 1 of the present invention was thus produced. FIG. 6(1) is a photograph of the tip section of the bubble-jetting member 1 produced in example 1. As is clear from the photograph, it could be confirmed that the inside of the extended section 4 was formed thick in a tapered form going toward the tip. Also, the diameter of the core 3 was about 30 μm, and the bubble jetting port 8 was circular having a diameter of about 6 μm.

Comparative Example 1

Stretched glass pulled apart without processing the tip section to be thick was used as a bubble-jetting member of comparative example 1. FIG. 6(2) is a photograph of the tip section of the bubble-jetting member 1 produced in comparative example 1. As is clear from the photograph, it could be confirmed that the entirety of the extended section 4 was thin and was formed in a tapered form. Also, the bubble-jetting port 8 was circular having a diameter of about 14 μm.

[Production of Localized Injection Device (Injection Device)]

Example 2

(1) Production of Outside Shell Part 13

A borosilicate glass tube for micropipettes (outer diameter 2.03 mm, inner diameter 1.68 mm, Drummond Scientific Company) was pulled apart under heating using a glass puller (product of Sutter Co., P-1000IVF). The pulled apart glass tube was set in a microforge (MF-900, Narishige Co.), and the tip was cut to a diameter of about 100 μm. Furthermore, constricted portions 14 were produced by placing the microforge in contact at a position about 300 μm back from the tip and heating four places at 90° intervals. The inner diameter of the tip section of the outside shell part 13 was about 100 μm.

(2) Assembly of Localized Injection Device

First, the bubble-jetting member 1 produced in example 1 was connected to an electric scalpel for medical use (product of ConMed Corp., 714-S) using Ag paste (H20E, Rikei Corp.). Then, the connection part was cured by heating on a hot plate at 120° C. for 15 minutes.

Next, PDMS (solvent: curing agent=25:1) (Dow Corning Toray Co., Ltd.) having been vacuum defoamed for 30 minutes was applied on an OHP film (Sumitomo 3M Ltd.), and spin coating was performed at 4000 rpm for 20 seconds. Then, the coated material was heat-cured in an oven at 120° C. for 60 minutes.

Figure 7:
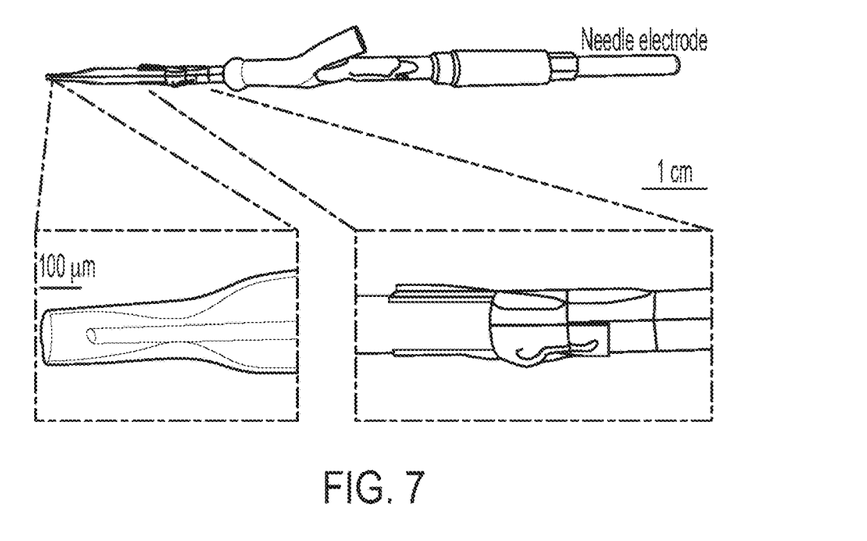
FIG. 7 is a photograph substituting for a drawing, and is an overall photograph of the localized injection device produced in example 2, as well as a photograph enlarging the tip section and the expansion/contraction section of the gas/liquid jetting member 10.

Also, a silicon tube (inner diameter 2 mm, outer diameter 3 mm) cut to about 2 cm was placed on a borosilicate glass tube for micropipettes (outer diameter 2.03 mm, inner diameter 1.68 mm, Drummond Scientific Company) cut to about 1.5 cm. A cut was furthermore made in the center of the silicon tube, and insertion was done from the cut portion up to the base of the bubble-jetting member 1, and joining was achieved with an adhesive agent (Super X, Cemedine Co., Ltd.) so that air does not leak. Finally, the outside shell part 13 produced in (1) was fitted on the outside of the bubble-jetting member 1, the abovementioned PDMS sheet produced previously was peeled from the OHP film with the end of the abovementioned glass tube cut to about 1.5 cm and the end of the outside shell part 13 being in positions away by about 3 mm, and the ends of the glass tube and the outside shell part 13 were joined together by wrapping, whereby the localized injection device of example 2 was produced. FIG. 7 is an overall photograph of the localized injection device produced in example 2, as well as a photograph enlarging the tip section and the expansion/contraction section of the gas/liquid jetting member 10.

Figure 8:
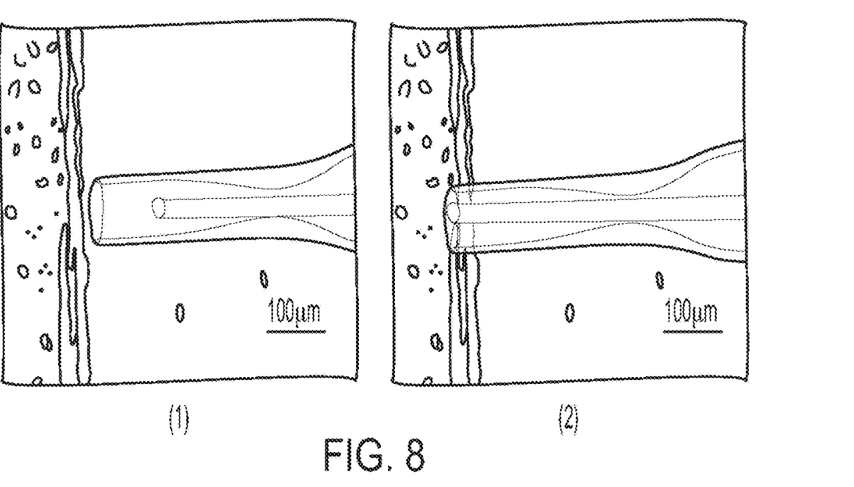
FIG. 8(1) is a photograph before pressing the tip of the localized injection device produced in example 2 against a process target, and FIG. 8(2) is a photograph after pressing the tip against the process target.

Also, FIG. 8 is a photograph of the movement of the tip section when using the localized injection device produced in example 2. FIG. 8(1) is a photograph before pressing the tip of the localized injection device produced in example 2 against a process target, and FIG. 8(2) is a photograph after pressing the tip against the process target. As is illustrated in FIG. 8, it was learned that the bubble-jetting member 1 and the outside shell part 13 are capable of relative movement, and the positional relationship of the bubble-jetting port 8 with a process target can be adjusted.

Example 3

(1) Production of Outside Shell Part 13

A borosilicate glass tube for micropipette (outer diameter 2.03 mm, inner diameter 1.68 mm, Drummond Scientific Company) was pulled using a glass puller (product of Sutter Co., P-1000IVF) while heating, a neck structure was created in the center, and both ends of the neck structure were cut to a suitable length, whereby an outside shell part 13 was produced. The inner diameter of the outside shell part 13 was about 1.6 mm.

(2) Assembly of Localized Injection Device

Next, PDMS (solvent:curing agent=10:1) (Dow Corning Toray Co., Ltd.) having been vacuum defoamed for 30 minutes was poured to a height of about 3 mm in a plastic tray of about 7 cm×7 cm×3 cm, vacuum defoaming was further performed for 20 minutes, and then the PDMS was baked for 20 minutes. Then the cured PDMS was removed from the plastic container and bored using a biopsy punch (Kai Corp.) having a hole diameter of 8 mm, the center was further bored using a biopsy punch (Kai Corp.) having a hole diameter of 2 mm, and a ring spacer was thus produced.

Figure 9:
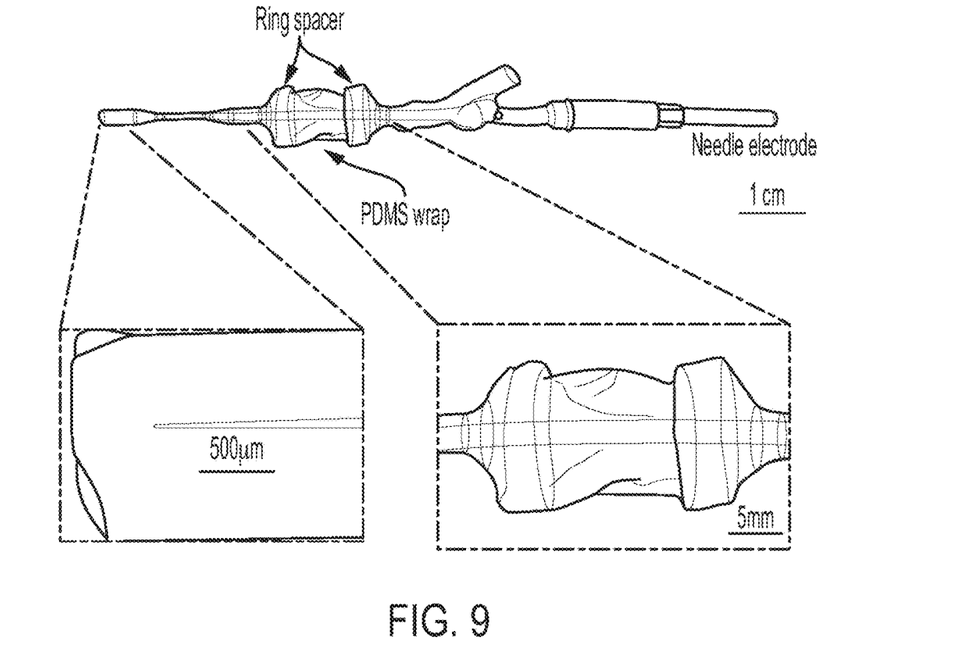
FIG. 9 is a photograph substituting for a drawing, and is an overall photograph of the localized injection device produced in example 3, as well as a photograph showing an enlargement of the tip section and the expansion/contraction section of the gas/liquid jetting member 10.

Next, a localized injection device was produced by the same procedure as in example 2, except that two ring spacers were separated by about 1 cm and the two ring spacers were wrapped by a PDMS sheet, instead of inserting the abovementioned ring spacer on the end of a glass tube cut to about 1.5 cm in procedure (2) in example 2 and inserting the abovementioned ring spacer on the end of the outside shell part 13, using the outside shell part 13 produced in example 3(1). FIG. 9 is an overall photograph of the localized injection device produced in example 3, as well as a photograph enlarging the tip section and the expansion/contraction section of the gas/liquid jetting member 10.

Comparative Example 2

A localized injection device was produced by the same procedure as in example 2, except that the bubble-jetting member of comparative example 1 was used instead of the bubble-jetting member 1 of example 2. The bubble-jetting port 8 and the outside shell part 13 were arranged to be about the same planar shape in order to allow the bubble-jetting port 8 to be close to a process target.

[Experiment on Strength of Tip of Bubble-Jetting Member 1]

Example 4

Figure 10:
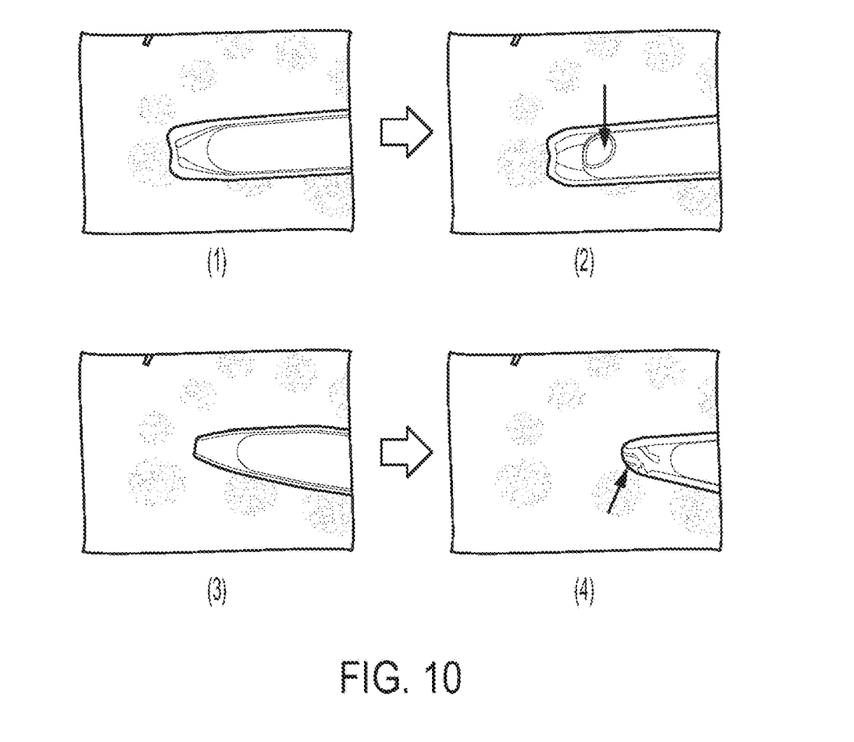
FIG. 10(1) is a photograph of the tip section of the bubble-jetting member 1 before applying power in example 4, FIG. 10(2) is a photograph of the tip section immediately after being damaged by application of power, FIG. 10(3) is a photograph of the tip section of the bubble-jetting member 1 before applying power in comparative example 3, and FIG. 10(4) is a photograph of the tip section immediately after being damaged by application of power.

The gas/liquid jetting member 10 of the localized injection device produced in example 3 and a counter electrode 22 produced with a copper plate were immersed in Steinberg solution (NaCl 3.4 g/L, KCl 0.05 g/L, $Ca(NO_3)_2 \cdot 4H_2O$ 0.08 g/L, $MgSO_4 \cdot 7H_2O$ 0.205 g/L, HEPES 0.715 g/L, ultrapure water 1 L). Next, the power applied to the core 3 and the counter electrode 22 was gradually increased, upon which the tip section of the bubble-jetting member 1 was damaged at about 8.80 mA and 2160 V. FIG. 10(1) is a photograph of the tip section of the bubble-jetting member 1 before applying power, and FIG. 10(2) is a photograph of the tip section immediately after being damaged by application of power. The arrow in FIG. 10(2) indicates the place of damage, and the shell part 5 was damaged in the vicinity of the boundary between the core 3 and the shell part 5.

Comparative Example 3

Power was applied in the same manner as in example 4, except that the localized injection device of comparative example 2 was used instead of the localized injection device of example 3, upon which the tip section of the bubble-jetting member 1 was damaged at about 5.33 mA and 1560 V. FIG. 10(3) is a photograph of the tip section of the bubble-jetting member 1 before applying power, and FIG. 10(4) is a photograph of the tip section immediately after being damaged by application of power. The arrow in FIG. 10(4) indicates the place of damage, and the tip section of the extended section 4 was damaged.

It was clear from the above results that the power applied to the bubble-jetting member 1 can be increased by forming a thick portion on the tip of the bubble-jetting member 1.

Experiment on Damage to Process Target by Localized Injection Device

Example 5

Figure 11:
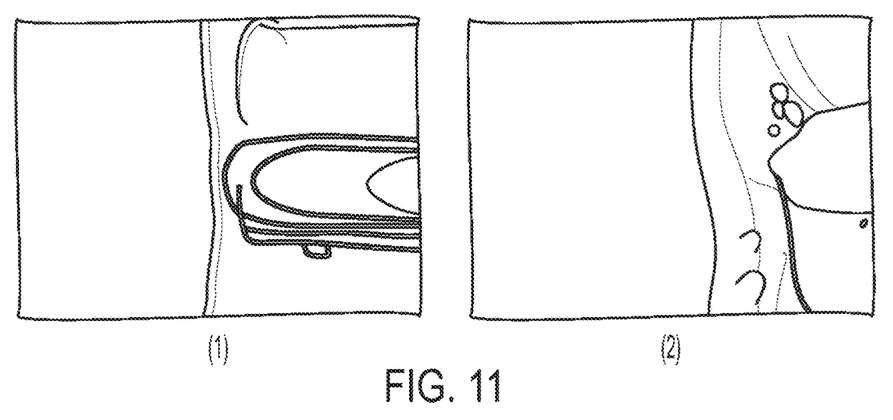
FIG. 11(1) is a photograph immediately after jetting bubbles on an unfertilized egg of *Xenopus laevus* in example 5, and FIG. 11(2) is a photograph immediately after jetting bubbles on an unfertilized egg of *Xenopus laevus* in comparative example 4.

The bubble-jetting port 8 (aperture 6 μm) of the localized injection device produced in example 2 was observed under microscope, the bubble jetting port was moved closer from the opposite side to an unfertilized egg of *Xenopus laevus* (referred to below as "unfertilized egg") fixed by egg forceps made of PDMS, and power of 1.8 mA and 440 V was next applied thereto. FIG. 11(1) is a photograph immediately after applying voltage and jetting bubbles. When bubbles were jetted on the unfertilized egg, the unfertilized egg was first pushed inward in the direction of progress of the bubbles by the collision energy of the bubbles, and when jetting of bubbles was stopped, the unfertilized egg was pushed back to the side of the bubble-jetting port 8 by the reaction and often came in contact with the bubble-jetting port 8. However, the tip of the bubble-jetting member 1 never adversely affected the unfertilized egg because the tip was flat.

Comparative Example 4

A bubble-jetting port 8 (aperture 14 μm) was moved closer to an unfertilized egg and power was applied thereto in the same manner as in example 5, except that the localized injection device produced in comparative example 2 was used. FIG. 11(2) is a photograph immediately after applying voltage and jetting bubbles. In comparative example 4, because the tip of the bubble-jetting member was sharp, the bubble-jetting port 8 pierced the unfertilized egg when the unfertilized egg was deformed on the side of the bubble-jetting port 8 by the reaction.

Example 6

Figure 12:
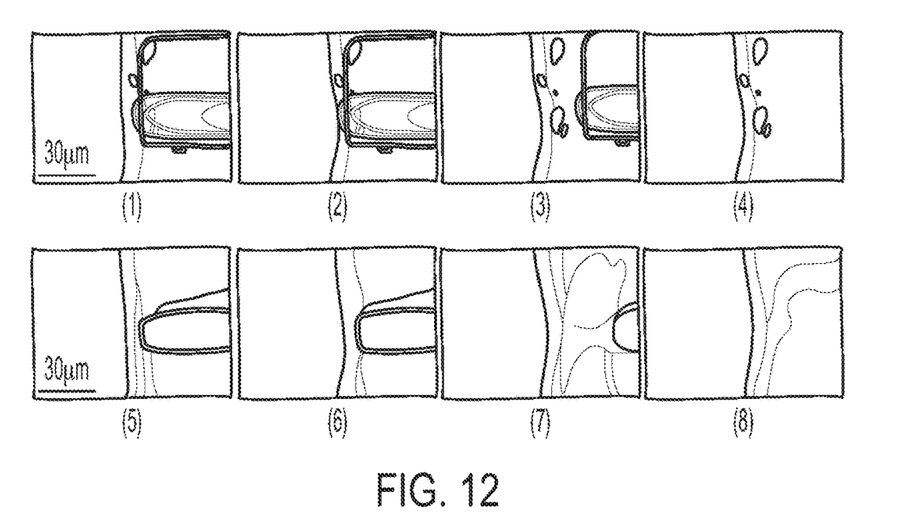
FIGS. 12(1) to (4) are photographs in time series when performing localized injection on an unfertilized egg of *Xenopus laevus* in example 6, and FIGS. 12(5) to (8) are photographs in time series when performing localized injection on an unfertilized egg of *Xenopus laevus* in comparative example 5.

It was confirmed that an unfertilized egg was not adversely affected during bubble jetting when the bubble-jetting member 1 of the present invention was used in example 5, but the effect on an unfertilized egg from a series of operations of localized injection was examined. In order to observe the extent of injuring of an unfertilized egg, a fluorescent reagent (Dextran, Alexa Fluor R 594, 10,000 MW; product of Life Technologies of Japan Ltd.) was added to a Steinberg solution. When an unfertilized egg is adversely affected and the contents leak to the outside, the fluorescent reagent bonds with the contents and visualization is possible. The rest of the procedure was carried out in the same manner as in example 5. FIG. 12(1) is a photograph before applying power (t=0 seconds), FIG. 12(2) is a photograph at the instant when power was applied and the jetted bubbles were brought to collide (t=0.3 seconds), FIG. 12(3) is a photograph immediately after the bubble-jetting port 8 was moved away from the unfertilized egg (t=5 seconds), and FIG. 12(4) is a photograph after 10 seconds elapsed after the bubbles were brought to collide.

Comparative Example 5

Power was applied by the same procedure as in example 6, except that the localized injection device produced in comparative example 2 was used. FIG. 12(5) is a photograph before applying power (t=0 seconds), FIG. 12(6) is a photograph at the instant when power was applied and the jetted bubbles were brought to collide (t=0.3 seconds), FIG. 12(7) is a photograph immediately after the bubble-jetting port 8 (aperture 14 μm) was moved away from the unfertilized egg (t=5 seconds), and FIG. 12(8) is a photograph after 10 seconds elapsed after the bubbles were brought to collide. As is clear from FIG. 12, it could be confirmed that the internals were ejected from the unfertilized egg when the conventional gas/liquid jetting member 10 was used. This is thought to be because the impact of collision of the bubbles on the unfertilized egg is high due to the large aperture of the bubble-jetting port 8 of the conventional gas/liquid jetting member 10, and also because the bubble-jetting port 8 may adversely affect the unfertilized egg during bubble jetting because the tip section of the bubble-jetting port 8 is made by drawing apart glass.

Meanwhile, when the localized injection device of the present invention is used, an unfertilized egg is unlikely to be adversely affected when the bubble-jetting port 8 is moved closer to the unfertilized egg because the tip section of the bubble-jetting member 1 has a thick and smooth shape. Furthermore, this is thought to be because the bubbles had a lesser impact when colliding with the unfertilized egg because the diameter of the bubble-jetting port 8 is smaller than the diameter of the conventional bubble-jetting member 1.

Figure 13:
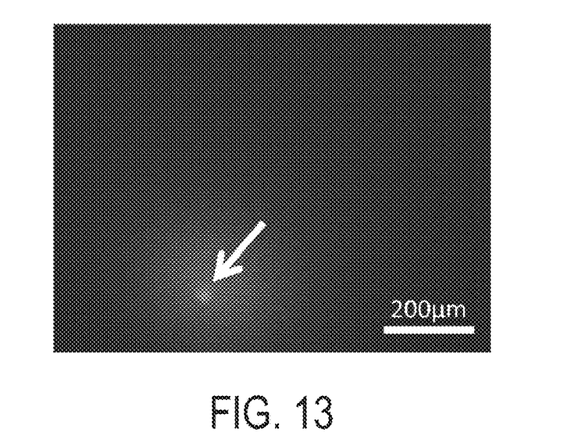
FIG. 13 is a photograph substituting for a drawing, and is a photograph taken by CCD camera of an unfertilized egg illuminated by mercury lamp 10 seconds after colliding with bubbles in example 6.

FIG. 13 is a photograph taken by CCD camera of an unfertilized egg illuminated by mercury lamp 10 seconds after colliding with bubbles in example 6. As is indicated by the arrow on the photograph in FIG. 13, it could be confirmed that the fluorescent reagent was locally injected. From the above results, it could be confirmed that localized injection could be performed while minimizing any adverse effect on the process target by using the localized injection device of the present invention.

[In-Air Injection Using Localized Injection Device (Injection Device)]

Example 7: Injection into Tomato

Figure 14:
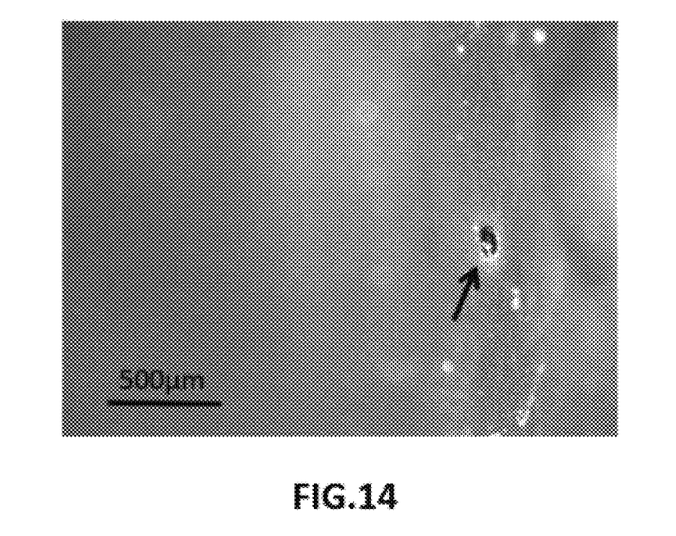
FIG. 14 is a photograph substituting for a drawing, and is a photograph of a tomato after performing localized injection in example 7.

A localized injection device was produced by the same procedure as in example 3 except that a bubble-jetting member 1 having a bubble-jetting port having a diameter of 4 μm was used. Next, the Steinberg solution of example 4 was filled into the outside shell part 13, and a tomato was pressed against. A counter electrode 22 was arranged to be in contact with the bottom of the tomato. Next, 1740 V of voltage was applied at 2.3 mA. FIG. 14 is a photograph of a tomato after localized injection, and the arrow portion is the place where the injection was performed.

Example 8: Localized Injection into Leaf of Radish Sprout

Figure 15:
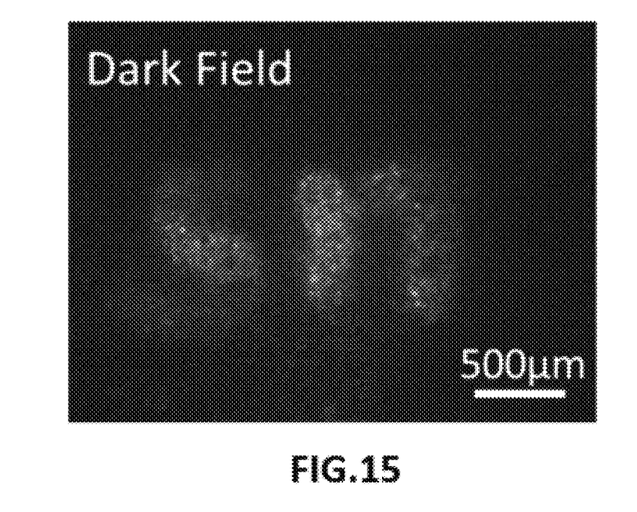
FIG. 15 is a photograph substituting for a drawing, and is a photograph in dark field of a leaf of a radish sprout after localized injection.

Pure water was filled inside the outside shell part 13 produced in example 3, and leaves of radish sprouts were pressed against. A fluorescent reagent (Fluorescein Isothiocyanate-Dextran (10,000 MW; product of SIGMA-Aldrich Corp.) was added to the pure water. Also, a counter electrode 22 was arranged on the underside of the leaves of radish sprouts. Next, 1.3 kV of voltage was applied at 81.8 mA. FIG. 15 is a photograph in dark field of leaves of radish sprouts after localized injection. As is illustrated in FIG. 15, because the fluorescent light could be confirmed, the fluorescent reagent could be injected into the leaves of radish sprouts.

Example 9: Localized Injection into Chicken Fillet

A bubble-jetting member 1 was produced by the same procedure as in example 1 except that Cu wire having a diameter of 100 μm was used instead of Cu wire having a diameter of 30 μm. The diameter of the core was about 100 μm, and the bubble-jetting port 8 was round with a diameter of about 6 μm. Next, a localized injection device was produced by the same procedure as in example 3 except that the produced bubble-jetting member 1 was used.

Figure 16:
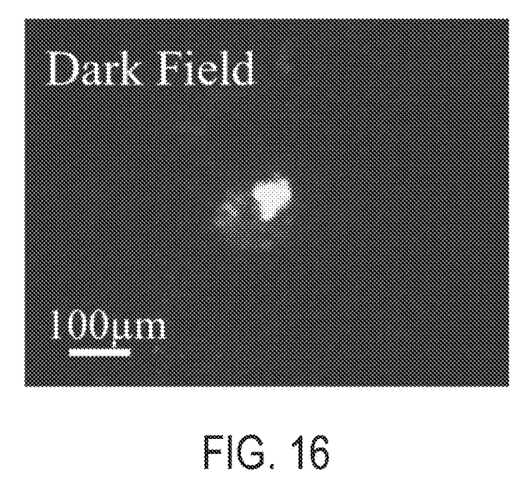
FIG. 16 is a photograph substituting for a drawing, and is a photograph in dark field of a chicken fillet after localized injection.

A NaCl solution (0.9% w/v) was filled into the outside shell part 13 of the produced localized injection device, and a chicken fillet was pressed against. Fluorescent beads (φ2.1 μm; product of Thermo Scientific Inc.) were added to the NaCl solution. The reason why fluorescent beads were used in example 9 was because the fluorescent reagent in example 8 permeated the chicken fillet. Also, a counter electrode 22 was placed beneath the chicken fillet. Next, 1.3 kV of voltage was applied at 200 mA. FIG. 16 is a photograph in dark field of chicken fillets after localized injection. As is illustrated in FIG. 16, the fluorescent beads could be locally injected into the chicken fillet.

Example 10: Injection into Brown Rice (Hulled)

Figure 17:
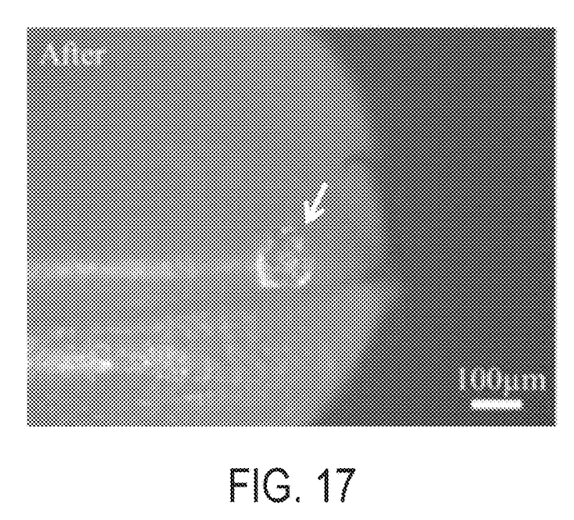
FIG. 17 a photograph substituting for a drawing, and is a photograph in dark field of brown rice after localized injection.

Localized injection was performed by the same procedure as in example 9, except that brown rice (hulled) was used instead of the chicken fillet, the brown rice was fixed on a jig made of PDMS, a counter electrode 22 was arranged to be in contact with a NaCl solution between the bubble-jetting member 1 and the outside shell part 13, and 1.8 kV of voltage was applied at 420 mA. FIG. 17 is a photograph in dark field of brown rice after localized injection. As is illustrated in FIG. 17, localized injection was possible into brown rice.

As is indicated in examples 7 to 10, it was confirmed that localized injection could be performed in process targets from soft to hard in open air when the localized injection device of the present invention is used.

[Production of Other Embodiments of Localized Injection Device (Injection Device)]

Example 11

Figure 18:
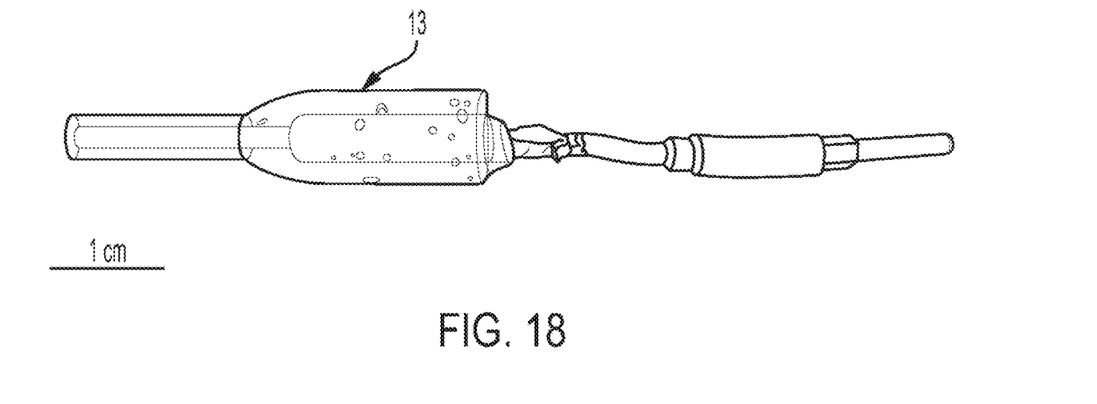
FIG. 18 is a photograph substituting for a drawing, and is a photograph showing an external view of the localized injection device produced in example 11, in another embodiment of the localized injection device of the present invention.

Instead of the outside shell part 13 of example 2, PDMS was transferred and molded into a three-dimensional shape using a plastic, glass, or metal rod to become in a hollow circular shape, whereby the entirety of the outside shell part 13 was made of PDMS. FIG. 18 is a photograph showing an external view of the produced localized injection device.

Figure 19:
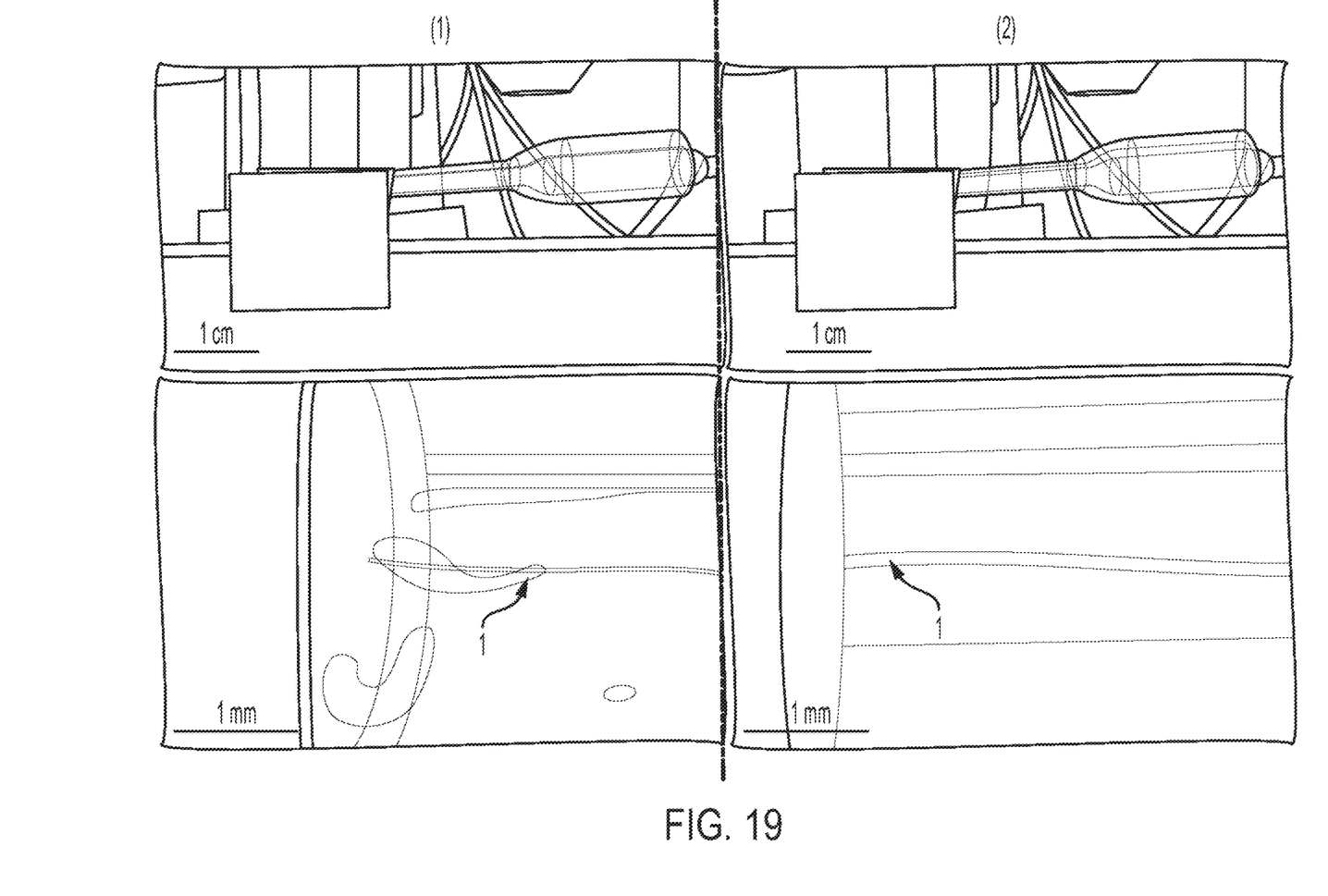
FIG. 19 is a photograph substituting for a drawing, and is a photograph showing the movement of the tip section of the localized injection device produced in example 8 of the present invention.

FIG. 19 is a photograph showing the movement of the tip section of the localized injection device produced in example 11. FIG. 19(1) is a photograph before pressing against an object, and FIG. 19(2) is a photograph after pressing against the object. Also, in FIGS. 19(1) and (2), the upper level is an overall photograph of the outside shell part 13, and the lower level is a photograph enlarging the tip section. As is clear from FIG. 19, it was learned that by forming the entirety of the outside shell part 13 using a flexible material, the bubble-jetting member 1 and the outside shell part 13 are capable of relative movement and the positional relationship between the process target and the bubble-jetting port 8 can be adjusted, even without using an expansion/contraction member 17.

INDUSTRIAL UTILITY

Process targets can be processed more finely than with the conventional techniques by using the bubble-jetting member, gas/liquid jetting member, localized ablation device, and localized injection device of the present invention. Furthermore, the localized injection device of the present invention can be used in atmospheric air, and can be used as a needleless injection device. Accordingly, use is possible in fine processing of process targets in medical institutions, universities, corporations, and other research and development institutions, etc., and use is possible also as a needleless injection device in metal institutions, organizations in livestock, agriculture, forestry, and fisheries, etc.

What is claimed is:

1. A gas/liquid jetting member, comprising a bubble-jetting member, and an outside shell part: wherein
   the bubble-jetting member comprises:
   a core formed of a conductive material and having a tip;
   a shell part formed of an insulating material, including an extended section extending beyond the tip of the core, and adheres at least partially to the core and covers the core, the extended section of the shell part having a tip including a bubble-jetting port; and
   a space formed between the extended section of the shell part and the tip of the core, and configured to receive a solution;
   the tip of the extended section of the shell part has a thick portion that is thicker than the rest of the extended section,
   the outside shell part at least partially encloses the shell part covering the core, the outside shell part having a tip section, the outside shell part and the shell part are spaced apart forming a space therebetween,
   an end of the outside shell part is connected to the bubble-jetting member by an expansion/contraction member, and
   the outside shell part and the bubble-jetting member are configured to be moveable relative to one another by the expansion/contraction member.

2. The gas/liquid jetting member according to claim 1, wherein a constricted portion is formed on the outside shell part, the constricted portion serving as a guide during relative movement between the outside shell part and the bubble-jetting member.

3. The gas/liquid jetting member according to claim 1, further comprising:
   a counter electrode formed on an outer surface of the shell part or on an inner surface of the outside shell part,
   wherein the core of the bubble-jetting member is an electrode, and together with the counter electrical constitutes a pair of electrodes.

4. The gas/liquid jetting member according to claim 1, wherein the tip section of the outside shell part is formed thicker than the rest of the outside shell part.

5. A localized injection device, comprising the gas/liquid jetting member according to claim 1.

6. The gas/liquid jetting member according to claim 2, further comprising:
   a counter electrode formed on an outer surface of the shell part or on an inner surface of the outside shell part,
   wherein the core of the bubble-jetting member is an electrode, and together with the counter electrical constitutes a pair of electrodes.

7. The gas/liquid jetting member according to claim 2, wherein the tip section of the outside shell part is formed thicker than the rest of the outside shell part.

8. A localized ablation device, comprising the gas/liquid jetting member according to claim 1.

* * * * *